United States Patent [19]
Hallan et al.

[11] Patent Number: 5,614,662
[45] Date of Patent: Mar. 25, 1997

[54] APPARATUS AND METHOD FOR MEASURING A PAPER SURFACE ROUGHNESS

[75] Inventors: Matthew J. Hallan, Savage, Minn.; Stephen J. Paradis, Los Altos Hills, Calif.; Donald F. Rogowski; Michael L. Shephard, both of Covington, Va.

[73] Assignee: Westvaco Corporation, New York, N.Y.

[21] Appl. No.: 352,893

[22] Filed: Dec. 9, 1994

Related U.S. Application Data

[63] Continuation-in-part of Ser. No. 10,760, Jan. 29, 1993, abandoned.

[51] Int. Cl.$^6$ .................................................. G01B 5/28
[52] U.S. Cl. ............................................. 73/105; 364/562
[58] Field of Search ................... 73/105, 159; 364/560, 364/562, 572, 576

[56] References Cited

U.S. PATENT DOCUMENTS

| | | |
|---|---|---|
| 3,470,739 | 10/1969 | Takafuji et al. . |
| 3,617,872 | 11/1971 | Horn et al. . |
| 3,720,818 | 3/1973 | Spragg et al. . |
| 4,106,333 | 8/1978 | Salje et al. . |
| 4,126,036 | 11/1978 | Nilan et al. . |
| 4,207,579 | 6/1980 | Gamblin et al. . |
| 4,433,386 | 2/1984 | Este . |
| 4,665,739 | 5/1987 | Mizuno . |
| 4,667,944 | 5/1987 | Althouse . |
| 4,669,300 | 6/1987 | Hall et al. . |
| 4,675,242 | 6/1987 | Hashimoto et al. . |
| 4,860,229 | 8/1989 | Abbe et al. ............................. 364/563 |
| 4,888,983 | 12/1989 | Dunfield et al. .......................... 73/105 |
| 5,118,195 | 6/1992 | Dobbie . |
| 5,125,746 | 6/1992 | Lipshitz ................................. 356/376 |
| 5,133,601 | 7/1992 | Cohen et al. . |
| 5,155,558 | 10/1992 | Tannenbaum et al. . |
| 5,208,766 | 5/1993 | Chang et al. ............................ 364/576 |
| 5,298,963 | 3/1994 | Moriya et al. ...................... 356/371 X |
| 5,301,129 | 5/1994 | McKaughan et al. .................. 364/552 |

FOREIGN PATENT DOCUMENTS

| | | |
|---|---|---|
| 57-74601 | 5/1982 | Japan . |
| 60-135708 | 7/1985 | Japan . |
| 62-75209 | 4/1987 | Japan . |
| 4-65619 | 3/1992 | Japan . |

OTHER PUBLICATIONS

"Multidimension Digital Signal Processing," by D. E. Dudgeon and R. M. Mersereau, Prentice–Hall, Inc. Englewood Cliffs, New Jersey, 1984.

Papier–Topographie mit dem Laser–Scanner, M. A. Gold und H. K. Schuster, Wochenblatt Fur Papierfabrikation 1989.

Form and Surface Texture Measurement, Rank Taylor Hobson, Form Talysurf Series.

*Primary Examiner*—Hezron E. Williams
*Assistant Examiner*—Daniel S. Larkin
*Attorney, Agent, or Firm*—J. R. McDaniel; R. L. Schmalz

[57] ABSTRACT

Subjective paper characteristics such as visual appearance and print quality are often objectively related to certain scales of surface roughness. Three dimensional topographic surface data is obtained from a paper sample secured by vacuum to a flat, porous plate for translational movement in a grid pattern beneath a vertically compliant stylus that is resiliently suspended beneath a rigid, overhead support beam. Such surface data is mathematically filtered by a linear convolution technique or the distinctly alternative circular convolution technique to segregate the raw data characteristics of component surfaces that contain only certain frequencies of roughness. The root-mean-square variations of such component surfaces is then used to objectively characterize respective surface characteristics.

9 Claims, 4 Drawing Sheets

APPARATUS AND METHOD FOR MEASURING A PAPER SURFACE ROUGHNESS

CROSS-REFERENCE TO RELATED APPLICATIONS

This application is a continuation-in-part of the commonly assigned, U.S. patent application Ser. No. 08/010,760 filed Jan. 29, 1993, now abandoned, entitled APPARATUS AND METHOD FOR MEASURING A PAPER SURFACE ROUGHNESS.

BACKGROUND OF THE INVENTION

1. Field of the Invention

The present invention generally relates to the analysis of paper surface qualities. More particularly, the invention relates to a method and apparatus for three dimensionally measuring and evaluating data descriptive of a paper surface topography.

2. Description of the Prior Art

As applied to paper, "print quality" is a subjective, human eye assessment of a particular paper surface respective to the printed product of that surface. One of the more influential objective factors bearing upon the print quality of a paper surface is the "roughness" of that surface. Additionally, paper is also subjectively appraised for simply unprinted visual surface smoothness. Consequently, numerous methods have been devised to measure the roughness of an unprinted paper surface as a predictor of the printed product.

Several widely used, indirect, methods of paper surface roughness measurement, characterized as Sheffield smoothness, Bekk smoothness and Parker Print Surf, include air leak techniques which measure the volume of air that leaks, over a fixed time interval, between the paper surface and a test equipment seal, or, conversely, the time required for the leakage of a fixed air volume. Although these indirect surface roughness measurement methods offer a numerically quantified, relative value of surface roughness, they have not proven to be consistent, reliable indicators of print quality.

Traditional surface roughness measurement relies upon the single, line trace of a stylus over the surface as is represented by U.S. Pat. No. 4,888,983 to L. G. Dunfield et al. Surface height values are measured at uniformly separated increments within a single, vertical evaluation plane. Such surface height values are digitized and processed algorithmically by Dunfield et al. to determine a corresponding print quality index.

Machine made paper, however, has a directional orientation relative to the machine production line. A greater percentage of papermaking fiber aligns with the machine direction than with the cross-machine direction. Extremely exaggerated, this circumstance of machine direction fiber alignment may be perceived as a corrugated topography. If measured by a single, vertical displacement stylus in a direction transversely of the corrugation ribs, the analysis would report a "rough" surface with large but highly regular vertical distance variations between the measured peaks and valleys. When measured in a direction parallel with the corrugation ribs, the analysis would report a "smooth" surface with small variations between vertical distance variations. Only by means of three dimensional measurement may the parallel ribbed nature of the surface be recognized.

From the foregoing illustration, it is demonstrated that a three dimensional topography is defined by length, width, and height coordinates, the length and width coordinates being in the same plane and the height coordinate measured perpendicularly from the length/width plane.

It is, therefore, an object of the present invention to provide a method and apparatus for quantifying the roughness quality of a paper surface based upon the three dimensional topography of the surface.

Another object of the present invention is to provide a method and apparatus for paper surface roughness measurement which accommodates the surface directionality.

Another object of the invention is to provide a digital characterization of a surface topography.

SUMMARY OF THE INVENTION

These and other objects of the invention to be subsequently explained are accomplished with an apparatus combination which includes sample holding means, sample positioning and drive means, stylus measuring means, and electronic data processing means. Paper samples are positionally secured by a regulated vacuum against a flat, porous surface. The porous surface is positionally adjusted in the X and Y directions of Cartesian coordinates in a horizontal plane by respective stepper motors.

An extremely sensitive vertical displacement measuring stylus is calibrated in position against the held sample surface. As the stepper motors drive the holder and sample through an equidistant grid pattern under the stylus, electrical analog signals are converted to digital values and stored in a unique address matrix. A digitized height measurement is recorded for each cell in an X—Y matrix wherein each cell is uniquely addressed to facilitate recovery of the surface height measured values in corresponding address related alignment.

The measured, raw data of a sample surface profile are electronically processed with selected digital filter matrices by linear convolution or circular convolution programs to produce a root-mean-square roughness value representative of the surface simulation of a selected filter frequency spectrum.

Multiple roughness values can be determined from a single raw data set by the use of distinctive digital filters.

DESCRIPTION OF THE DRAWINGS

Relative to the drawings wherein like reference characters designate like or similar elements throughout the several Figures of the drawings.

DESCRIPTION OF THE PREFERRED EMBODIMENT

Figure 1:
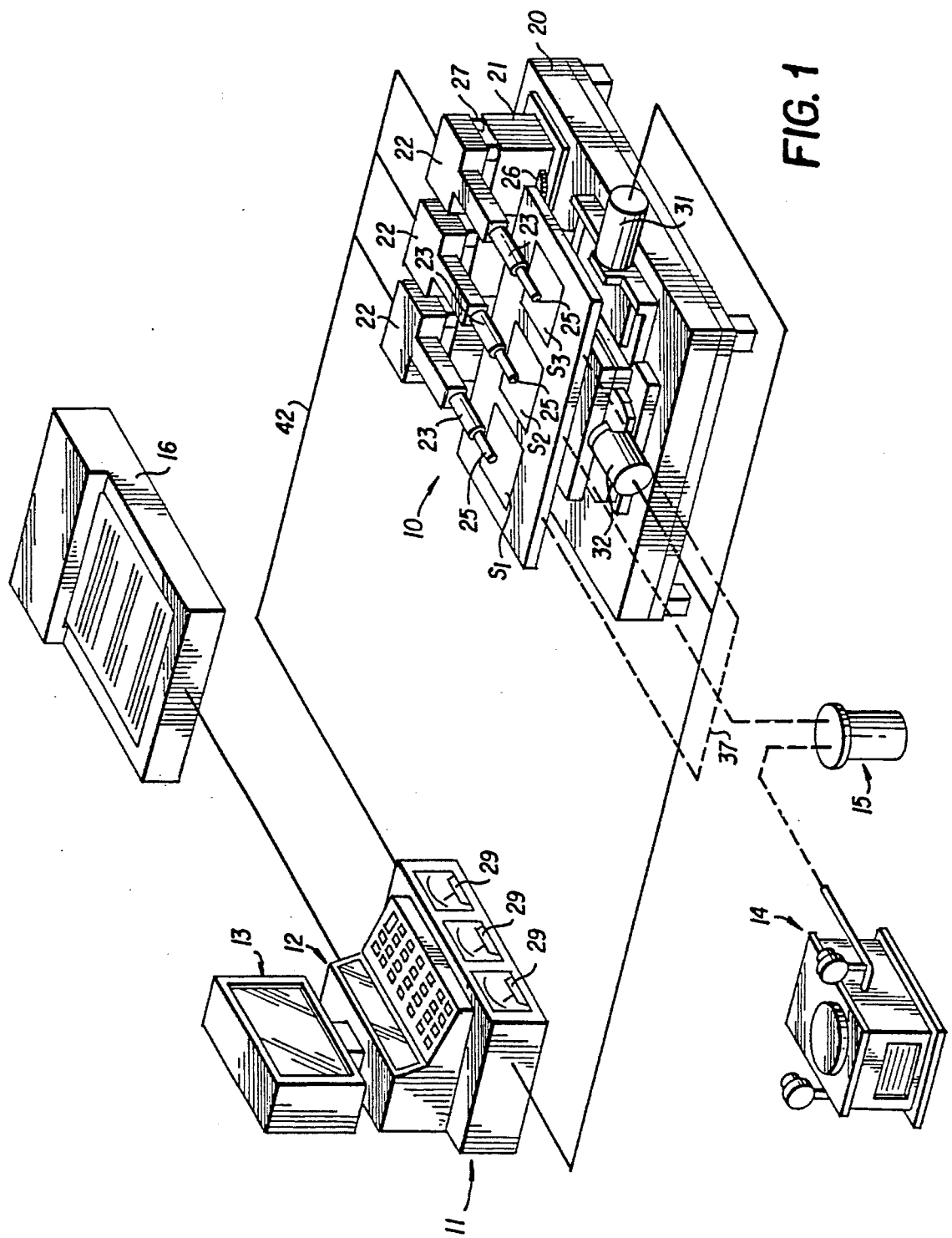
FIG. 1 is a pictorial schematic of the invention physical components.

The basic structural components of the present invention are illustrated pictorially by FIG. 1 to include the cooperative assembly of a sample survey unit 10, a digital data processing computer 11, a keyboard control console 12, a monitor 13, a vacuum pump 14, a regulated vacuum reservoir 15 and a printer 16.

The sample survey unit 10 comprises a massive support table 20 having one or more stylus support units 21. Each support unit carries a vertically adjustable stylus head 22 which supports a rigid stylus arm 23. The stylus per se 25 may be an article such as described in detail by U.S. Pat. No. 4,669,300 issued Jun. 2, 1987 to P. H. Hall et al. Typical stylus specifications would include a 0.0001 inch/2.53 μm diamond point radius for use on "fine" or writing paper and a 0.010 inch/0.25 mm carbide ball point radius for bleached paperboard.

Manual rotation of a jack wheel 26 causes a vertical displacement of the stylus head 22 within guide tubes 27 to calibrate the stylus 25 midpoint relative to the plane of a sample sheet $S_1$, $S_2$, or $S_3$.

Each sample sheet S is secured to the surface of a Cartesian coordinate table 30 (FIG. 4) by means of a vacuum system. Translational movement of the table 30 is directed by the computer 11 acting upon stepper motors 31 and 32. Upon a signal from the computer, one or both motors 31 or 32 will respond to the stepper motor driver 33 (FIG. 2) with a predetermined angle of rotation to translate the position of table 30 in mutually perpendicular directions under the stylus arms 23 to trace a transversely progressing series of parallel paths, each path having a predetermined number of stop point positions at regular spacings to define a grid pattern of equidistantly separated survey measuring points as illustrated by the trace pattern of FIG. 3. In the presently preferred embodiment of the invention, a grid of 256 parallel paths, each 1.6 inches long, spaced over a 1.6 inch distance are each provided with 256 survey data points along respective 1.6 inch lengths i.e. $(256)^2$ equidistantly spaced data points.

The spacing of these data points may be changed to resolve frequency ranges descriptively characteristic of the roughness scale under examination. The maximum frequency that can be resolved is equal to one-half the data point spacing frequency.

To secure the position of thin light weight samples such as paper, the Cartesian coordinate table 30 is provided with one or more vacuum sinks 35 (FIG. 4) covered by a porous metal plate 36 that has been machined to a specified flatness. The plate 36 pore size is selected to allow air to move through the plate without deforming the sample into the sinks. An example is a 10 micron pore size metal gas filter plate machined to a flatness of ±0.001 from Mott Metallurgical Corp., Farmington, CT.

Below the plate 36, the sink 35 is evacuated by a conduit system 37 connected to a vacuum source such as a pump 14. However, within the conduit system 37, between the sink 35 and the pump 14, is provided a regulated vacuum reservoir 15 sized to dampen any vacuum pulsations originating from the vacuum source.

Figure 2:
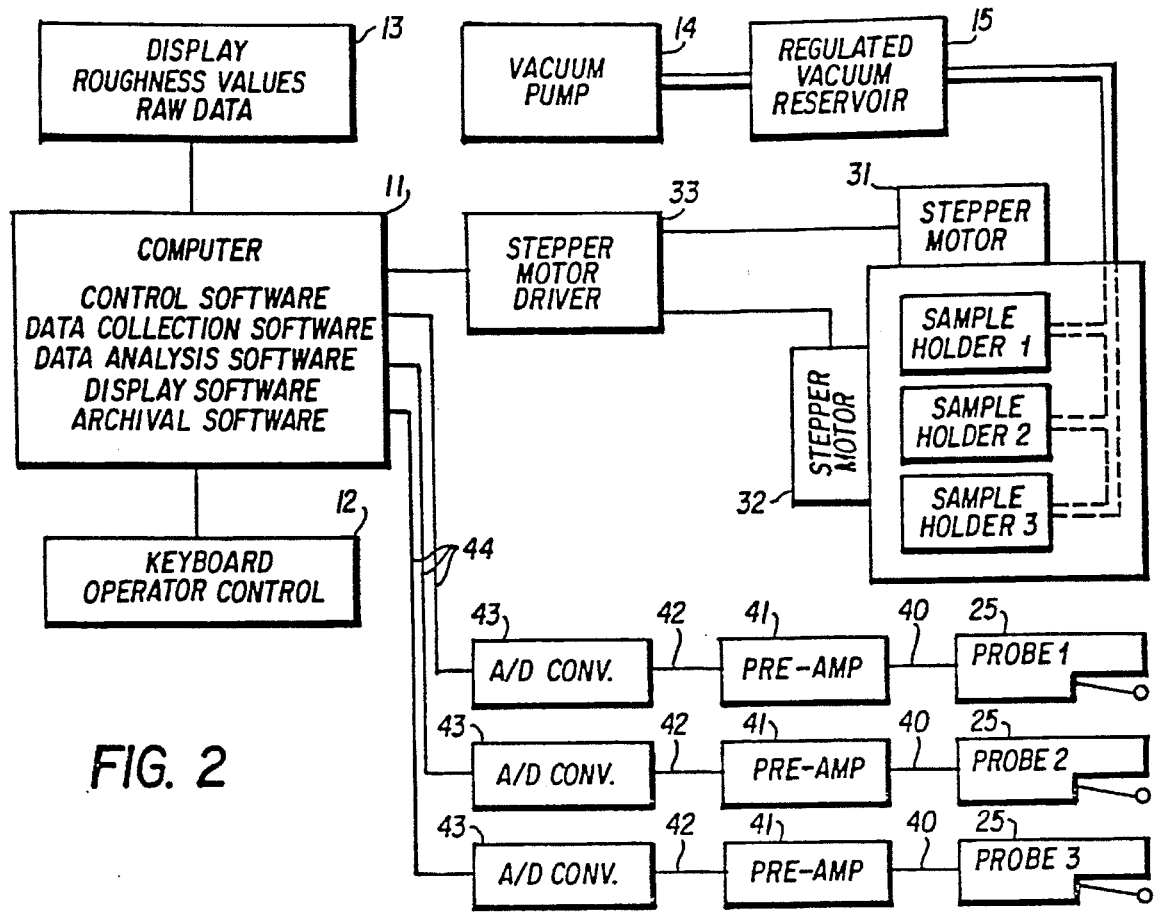
FIG. 2 is a line and block schematic of the invention.

To complete the system's physical description relative to FIG. 2, each analog signal 40 of stylus .25 is amplified by a power boosting preamplifier circuit 41. The amplified stylus analog signal 42 is subsequently transmitted to an analog-to-digital conversion circuit 43 for the production of corresponding digital data signals 44 in a suitable response form of computer 11.

Figure 4:
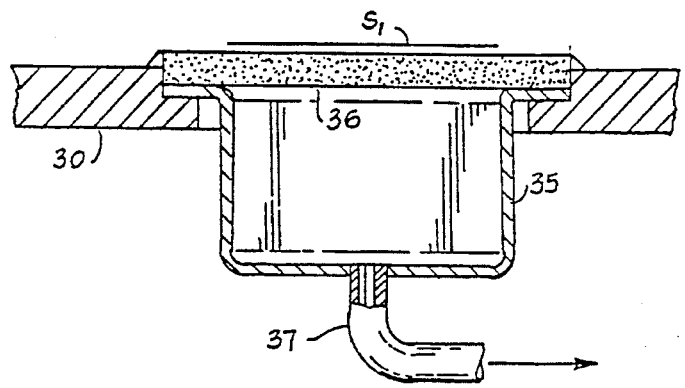
FIG. 4 is a sectioned detail of the invention sample mounting apparatus.

A sheet roughness determination procedure begins with placement of one or more sample sheets $S_1$, $S_2$, or $S_3$ on respective sample holders 36 of table 30 (FIG. 4). The stylus displacement probes 25 are placed onto the sample surfaces by manual manipulation of jack wheels 26 and adjusted to the mid-point of the probe displacement range.

Figure 3:
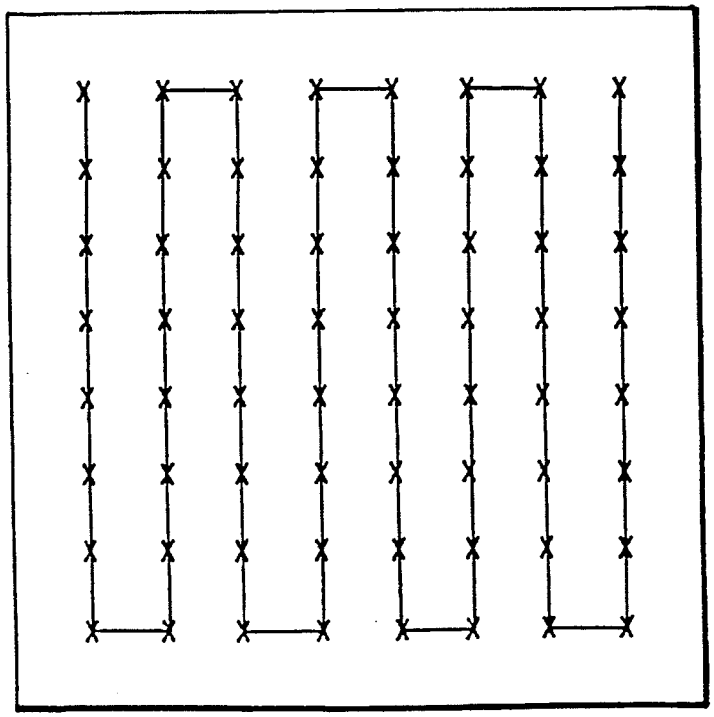
FIG. 3 is a trace pattern of the invention sample table movement.
Figure 5:
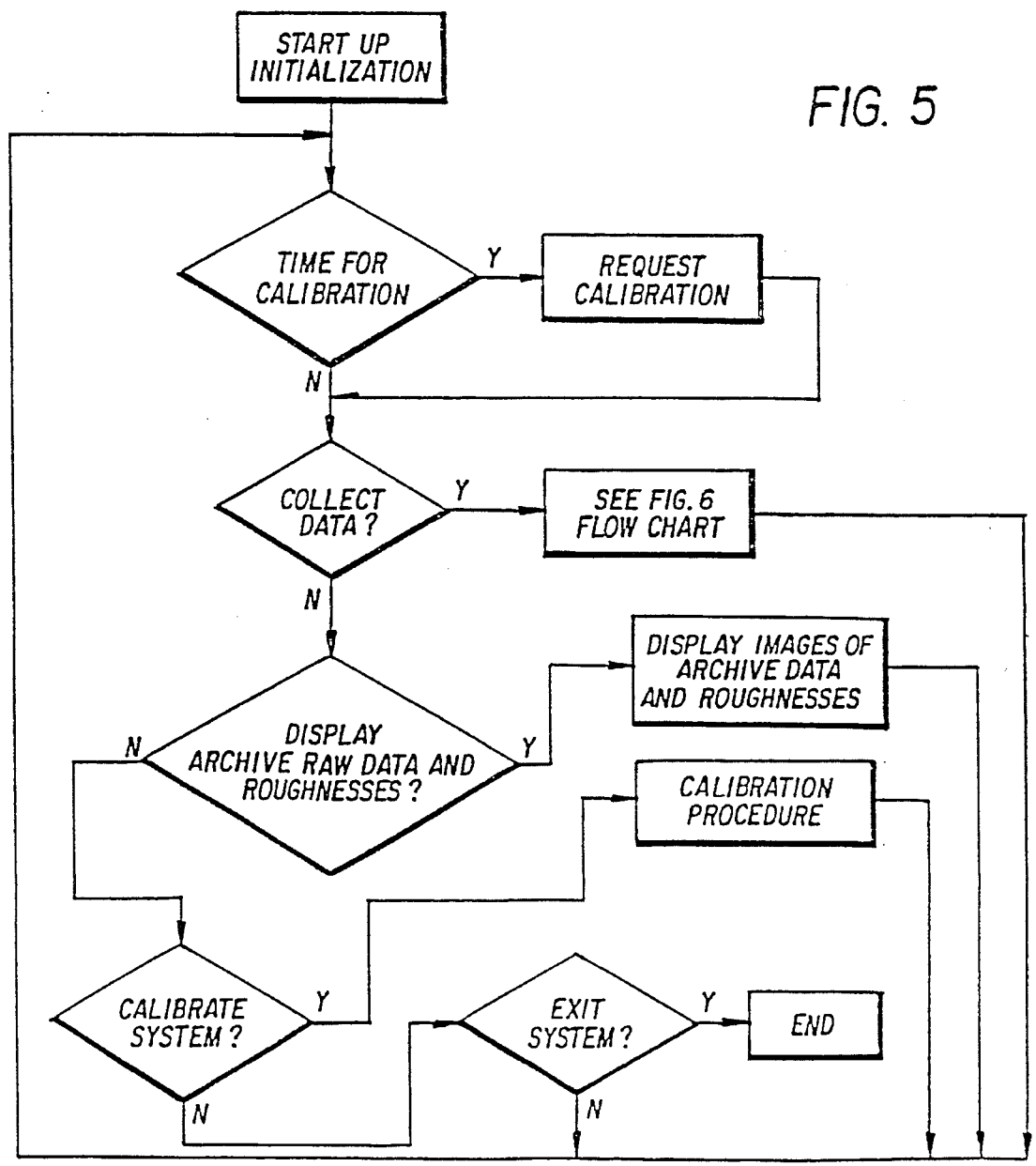
FIG. 5 is a block flow chart of the computer software control program applicable to the invention.
Figure 6:
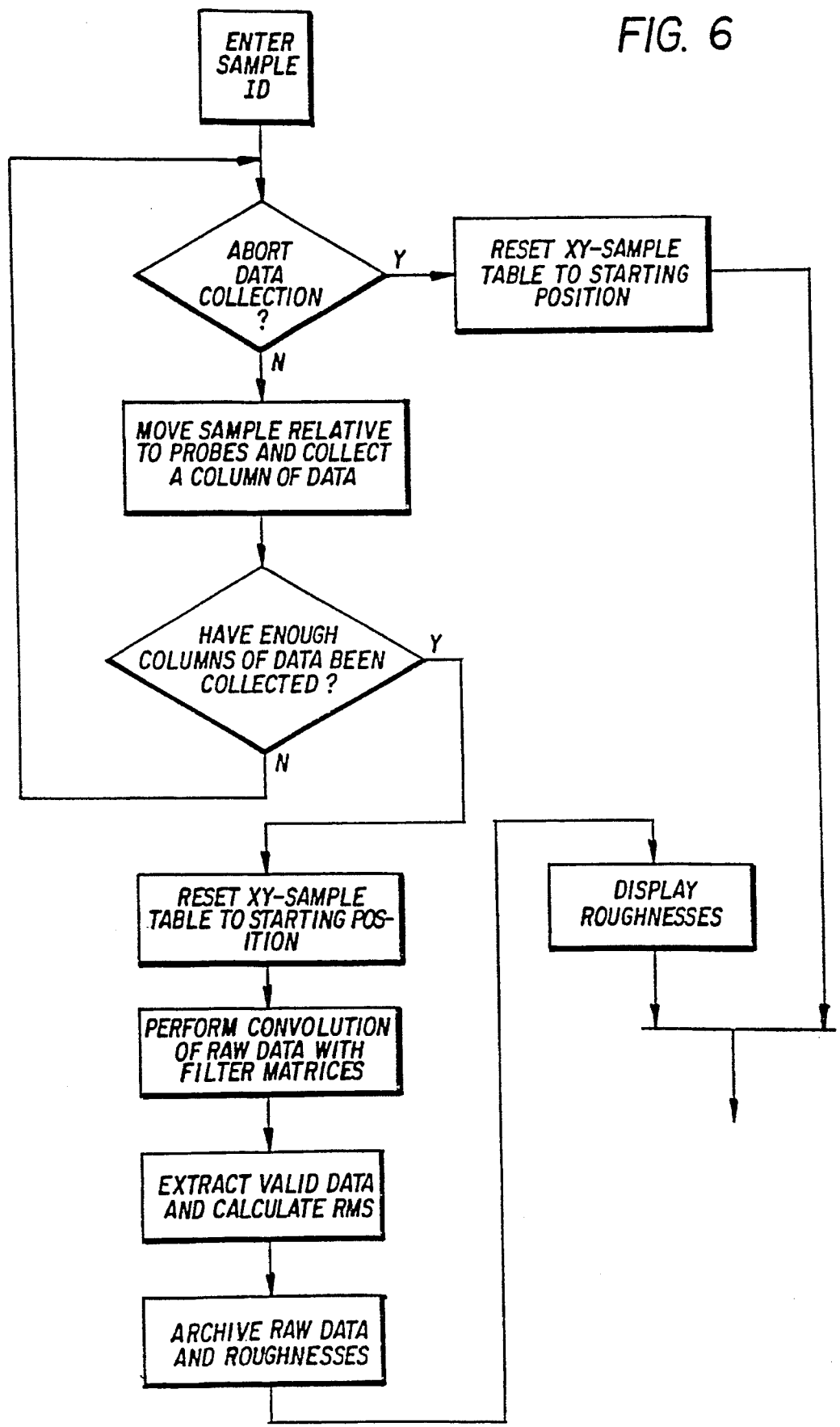
FIG. 6 is a block flow chart of the data analysis subroutine referenced in the flow chart of FIG. 5.

With reference to the software function flow chart of FIGS. 5 and 6, survey data collection begins with movement of Cartesian coordinate table 30 along the prescribed FIG. 3 path, giving pause at each data point to minimize the presence of mechanical movement noise in the signal system. The digital values produced by the A/D converters 43 (FIG. 2) are stored in correspondence with their respective matrix address. This process is repeated until the prescribed data course is completed.

Those of ordinary skill in the art will recognize that the mechanical stylus type of measuring device described herein may be alternatively replaced by an optical or other suitable measuring device.

Upon completion of the raw data matrix set, the correspondingly stored data are convoluted with a two-dimensional, finite-extent impulse response (FIR), or nonrecursive, zero-phase band-pass, digital filter that has been multiplied by a window function such as a circular Kaiser window. Alternatively, the raw data may be convoluted as accumulated and then stored for further or subsequent processing. The FIR filter that has been multiplied with the window was constructed and stored in the computer memory before the data collection procedure. Resultantly, the filter/window combination is retrieved from the memory for convolution. The FIR filter and window are designed using standard mathematical procedures that are described in "Multidimensional Digital Signal Processing" by D. E. Dudgeon and R. M. Mersereau, Prentice-Hall, 1984, pages 29–31 and pages 118–124. The choice of the filter cut off parameters is based upon the scale of roughness that one is interested in quantifying. The quantified scale of roughness is dependent upon the subjective quality of property one is attempting to quantify. Implementation of the convolution process is described by Dudgeon and Mersereau at pages 113–118.

The resultant matrix for each convolution of the raw data will contain both "good" and "bad" data. The "good" data are extracted from the resultant matrix of each convolution and then the root-mean-square roughness of this "good" data is determined and presented to the operator via the monitor 13 display or a printer 16 (FIG. 1).

Those of ordinary skill in the art will recognize that the root-mean-square roughness parameter for calculating a roughness value described herein may be alternatively replaced by another roughness parameter, such as, average roughness.

To describe this mathematical manipulation more graphically, the raw data represented by the relative height values at the matrix measuring points may be reduced to a single, root-mean-square value. However, this value does not usually correspond with the subjective evaluations of artists and experts. To derive a root-mean-square value for a specific type of paper that does correspond with the subjective evaluations of experts, a statistically sufficient number of unprinted and/or printed examples on samples of a specific paper type are comparatively graded by experts. Necessarily, this will be a subjective, visual, manual grading. Unprinted or printed examples of the same specific paper type are evaluated by the present invention to identify a constituent surface frequency or frequency spectrum that, when reduced to a root-mean-square value, corresponds with the subjective evaluation of experts. Once the relevant frequency or spectrum is identified for a specific type of paper, all subsequently produced quantities of this specific paper type may be graded by the root-mean-square value of that frequency or frequency range.

Regressing, the data matrix representing a raw sample surface within the test area is mathematically restructured into several constituent surface simulations; each conforming to a particular surface profile frequency range within a spectrum of such particular frequencies. Collectively, the full frequency spectrum of such surface simulations add up to the original, raw data surface.

Convoluted upon this spectral range of surface simulations is a mathematical filter derived from the references given above. By this model, selected surface frequencies or subspectrum are isolated from the whole surface spectrum for comparative relevance to subjective manual appraisals. Thereby, a signature frequency or subspectrum is identified for subsequent application to any example of the analyzed paper type.

For the presently preferred embodiment of the invention, raw data for each sheet sample are convoluted at least once, each time with a different filter. Other embodiments may convolute the raw data with fewer or more filters and thus produce fewer or more roughness values with one roughness value being determined for each filter used in a convolution.

Having fully disclosed our invention,
We claim:

1. An apparatus for surveying the surface topography of a sheet of material comprising:
    a sheet of material sample;
    a sample supporting table means having a selectively driven movement of a table surface along a constant surface plane, said table surface including a sample mounting area provided by a porous structural plate means covering a movable vacuum sink volume served by a vacuum source such that said sample is substantially stationary with respect to said plate means and said plate means is substantially stationary with respect to said vacuum sink volume;
    a sample surface point height measuring means secured substantially above said sample mounting area for generating electrical signals proportional to sample surface topography variations wherein said height measuring means is a stylus for emitting analog electrical signals that are proportional to vertical displacement distances traversed by a stylus, said analog signals being converted to digital signals for analysis wherein said stylus means is manually adjusted to a mid-range analog signal calibration scale in surface contact with a material sample; and,
    a control means for driving said table means in a grid pattern of equidistantly separated sample surface measuring points beneath said height measuring means.

2. An apparatus, as described by claim 1, wherein said porous plate means includes pores of about 10 microns and less.

3. An apparatus, as described by claim 1, wherein a sample supporting surface portion of said porous plate has a flatness tolerance of ±1 mil.

4. An apparatus, as described by claim 1, wherein a regulated vacuum reservoir is provided in conduit communication between said vacuum sink and said vacuum source.

5. An apparatus, as described by claim 1, wherein said table means is driven along Cartesian coordinates.

6. An apparatus, as described by claim 5, wherein said table means is driven by individually controlled stepper motors in respective Cartesian directions.

7. An apparatus, as described by claim 1, wherein said control means drives said table along a predetermined number of parallel paths advancing serially under said height measuring means and stops said table at points along each path substantially equal to the separation distance between parallel paths whereby said table stopping points under said height measuring means collectively form an equidistant grid matrix.

8. An apparatus, as described by claim 7 wherein the predetermined number of parallel paths correspond with the number of stopping points along a path whereby said grid matrix is square.

9. A method of objectively evaluating a surface quality comprising the steps of:
    preparing a plurality of samples having a range of surface qualities;
    manually evaluating and relatively grading said plurality of samples for said surface qualities;
    computationally evaluating and relatively grading said plurality of samples for surface qualities, wherein said computationally evaluating step is further comprised of the steps of;
    generating analog electrical signals proportional to height variation measurements taken from each sample surface at a multiplicity of equidistantly separated points distributed over an area grid, each point being uniquely characterized by an address value;
    converting said analog signals to corresponding digital height value signals for computer storage with coordinate grid point address values;
    entering said digital value signals and coordinate grid point address values in a computer data base for subsequent retrieval and processing;
    preparing a finite-impulse response data filter matrix for a plurality of frequencies distributed over a frequency spectrum;
    entering said data filter matrix in said computer data base;
    retrieving said height values for convolution by said computer with said filter matrix frequency spectrum to produce a convoluted data matrix respective to each of said plurality of frequencies within said spectrum;
    developing root-mean-square values from said convoluted data matrix respective to each of said plurality of frequencies within said spectrum to determine computational evaluations of said paper sample surface qualities; and,
    comparing an agreement coincidence between said manual evaluations of said samples and said computational evaluations of said samples.

* * * * *

UNITED STATES PATENT AND TRADEMARK OFFICE
CERTIFICATE OF CORRECTION

PATENT NO. : 5,614,662
DATED : Mar. 25, 1997
INVENTOR(S) : Matthew J. Hallan, Stephen J. Paradis, Donald F. Rogowski and Michael L. Shepard It is certified that error appears in the above-indentified patent and that said Letters Patent is hereby corrected as shown below:

Title page, item [75] Inventors: change "Shephard" to --Shepard--.

Col. 3, ln. 58, before --25-- delete "." .

Signed and Sealed this

Seventeenth Day of June, 1997

Attest:

BRUCE LEHMAN

*Attesting Officer*    *Commissioner of Patents and Trademarks*